United States Patent [19]

Clauss et al.

[11] Patent Number: 4,638,063

[45] Date of Patent: * Jan. 20, 1987

[54] PROCESS FOR THE PREPARATION OF 6-METHYL-3,4-DIHYDRO-1,2,3-OXATHIAZIN-4-ONE 2,2-DIOXIDE AND ITS NON-TOXIC SALTS

[75] Inventors: Karl Clauss, Kelkheim; Adolf Linkies, Frankfurt am Main; Dieter Reuschling, Butzbach, all of Fed. Rep. of Germany

[73] Assignee: Hoechst Aktiengesellschaft, Frankfurt, Fed. Rep. of Germany

[ * ] Notice: The portion of the term of this patent subsequent to Jan. 7, 2003 has been disclaimed.

[21] Appl. No.: 799,622

[22] Filed: Nov. 19, 1985

Related U.S. Application Data

[63] Continuation of Ser. No. 714,175, Mar. 20, 1985, Pat. No. 4,563,521.

[30] Foreign Application Priority Data

Mar. 22, 1984 [DE] Fed. Rep. of Germany ....... 3410440

[51] Int. Cl.⁴ .......................................... C07D 291/06
[52] U.S. Cl. ...................................................... 544/2
[58] Field of Search ............................................ 544/2

[56] References Cited

U.S. PATENT DOCUMENTS

| | | | |
|---|---|---|---|
| 3,689,486 | 9/1972 | Clauss et al. | 544/2 |
| 3,917,589 | 11/1975 | Clauss et al. | 544/2 |
| 3,926,976 | 12/1975 | Clauss et al. | 544/2 |
| 3,926,981 | 12/1975 | Clauss et al. | 544/2 |

*Primary Examiner*—John M. Ford
*Attorney, Agent, or Firm*—Curtis, Morris & Safford

[57] ABSTRACT

6-Methyl-3,4-dihydro-1,2,3-oxathiazin-4-one 2,2-dioxide is prepared by reaction of acetoacetamide with at least approximately twice the molar amount of $SO_3$ per mole of acetoacetamide, if appropriate in an inert inorganic or organic solvent. Relevant salts can be obtained, using bases, from the product which results in the form of the acid.

The non-toxic salts, in particular the potassium salt, are valuable synthetic sweeteners.

12 Claims, No Drawings

PROCESS FOR THE PREPARATION OF 6-METHYL-3,4-DIHYDRO-1,2,3-OXATHIAZIN-4-ONE 2,2-DIOXIDE AND ITS NON-TOXIC SALTS

This application is a continuation of application Ser. No. 714,175, filed Mar. 20, 1985, now U.S. Pat. No. 4,563,521.

6-Methyl-3,4-dihydro-1,2,3-oxathiazin-4-one 2,2dioxide is the compound of the formula

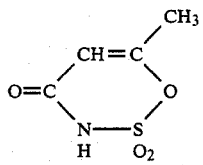

As a consequence of the acidic hydrogen on the nitrogen atom, the compound is able to form salts (with bases). The non-toxic salts, such as, for example, the Na, the K and the Ca salt, can, because of their sweet taste, which is intense in some cases, be used as sweeteners in the foodstuffs sector, the K salt ("Acesulfame K" or just "Acesulfame") being of particular importance.

A number of different processes is known for the preparation of 6-methyl-3,4-dihydro-1,2,3-oxathiazin-4-one 2,2-dioxide and its non-toxic salts; see Angewandte Chemie 8,5, Issue 22 (1973) pages 965 to 73, corresponding to International Edition Vol. 12, No. 11 (1973), pages 869-76. Virtually all the processes start from chloro- or fluorosulfonyl isocyanate (XSO$_2$NCO with X=Cl or F). The chloro- or fluorosulfonyl isocyanate is then reacted with monomethylacetylene, acetone, acetoacetic acid, tert.butyl acetoacetate or benzyl propenyl ether (usually in a multistage reaction) to give acetoacetamide-N-sulfonyl chloride or fluoride which, under the action of bases (such as, for example, methanolic KOH), is cyclized and provides the corresponding salts of 6-methyl-3,4-dihydro-1,2,3-oxathiazin-4-one 2,2-dioxide. Where desired, the free oxathiazinone can be obtained from the salts in a customary manner (with acids).

Another process for the preparation of the oxathiazinone intermediate acetoacetamide-N-sulfonyl fluoride starts from sulfamoyl fluoride H$_2$NSO$_2$F, which is the partial hydrolysis product of fluorosulfonyl isocyanate (German Offenlegunqsschrift No. 2,453,063). The fluoride of sulfamic acid H$_2$NSO$_2$F is then reacted with an approximately equimolar amount of the acetoacetylating agent diketene, in an inert organic solvent, in the presence of an amine, at temperatures between about −30° and 100° C.; the reaction takes place in accordance with the following equation (with triethylamine as the amine):

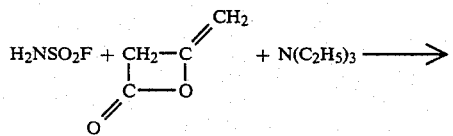

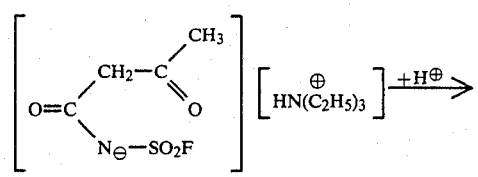

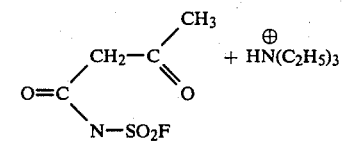

Acetoacetamide-N-sulfonyl fluoride

The acetoacetamide-N-sulfonyl fluoride is then cyclized in a customary manner using a base, for example using methanolic KOH, to the sweetener:

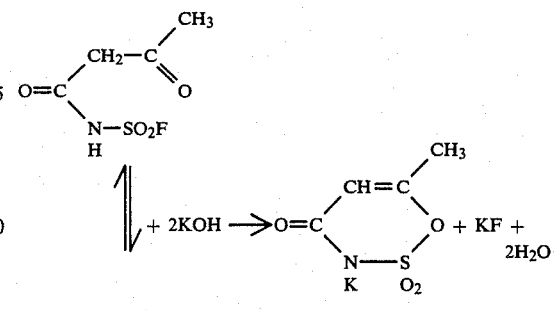

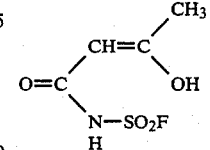

Although some of the known processes provide quite satisfactory yields of 6-methyl-3,4-dihydro-1,2,3-oxathiazin-4-one 2,2-dioxide and its non-toxic salts (up to about 85% of theory based on the starting sulfamoyl halide), they are still in need of improvement, particularly for industrial purposes, because of the necessity of using chloro- or fluorosulfonyl isocyanate, which are not very easy to obtain, as starting materials; this is because the preparation of the chloro- and fluorosulfonyl isocyanate requires considerable precautionary measures and safety arrangements by reason of the starting materials (HCN, Cl$_2$, SO$_3$ and HF), some of which are rather unpleasant to handle. The preparation of the chloro- and fluorosulfonyl isocyanate are based on the following reaction equations:

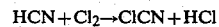

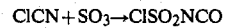

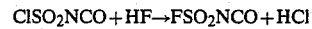

Replacement of the sulfamoyl fluoride in the process according to the abovementioned German Offenlegungsschrift No. 2,453,063 by, for example, the considerably more easily obtainable (for example from NH$_3$+SO$_3$) sulfamic acid H$_2$NSO$_3$H or its salts hardly appeared promising because the reaction of Na sulfamate H$_2$NSO$_3$Na with diketene in an aqueous-alkaline solution does not provide any reaction product which can be isolated pure. Rather, it has been possible to obtain the 1:1 adduct, which is probably at least partially formed in this reaction, only in the form of the coupling product with 4-nitrophenyldiazonium chloride, as a pale yellow dyestuff; see Ber. 83 (1950), pages 551–558, in particular page 555, last paragraph before the description of the experiments, and page 558, last paragraph:

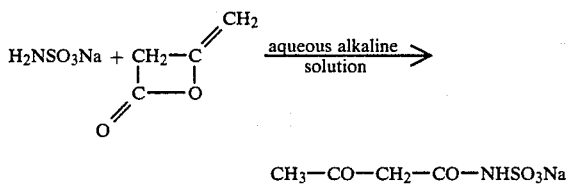

Moreover, the acetoacetamide-N-sulfonic acid has otherwise been postulated only, or also, as an intermediate in the decomposition of 6-methyl-3,4-dihydro-1,2,3-oxathiazin-4-one 2,2-dioxide during boiling in aqueous solution; see the literature cited in the introduction, Angew. Chemie (1973) loc. cit.:

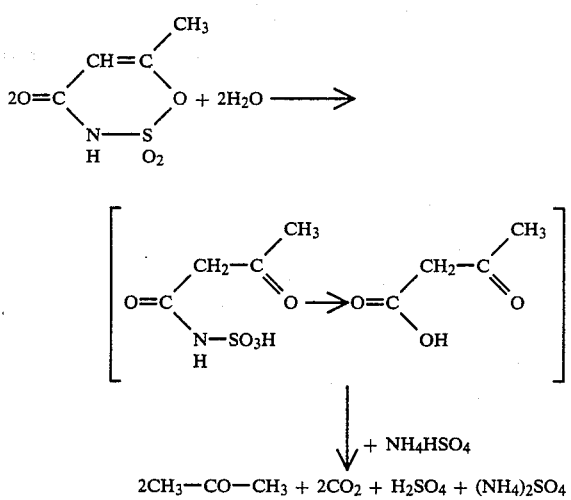

Thus, because the state of the art processes for the preparation of 6-methyl-3,4-dihydro-1,2,3-oxathiazin-4-one 2,2-dioxide and its non-toxic salts are, in particular, not entirely satisfactory for being carried out on an industrial scale, in particular as a result of the necessity to use starting materials which are not very straightforward to obtain, the object was to improve the known processes appropriately or to develop a new improved process.

This object has been achieved according to the invention by the reaction of acetoacetamide with at least aporoximately twice the molar amount of SO$_3$.

Thus, the invention relates to a process for the preparation of 6-methyl-3,4-dihydro-1,2,3-oxathiazin-4-one 2,2-dioxide and its non-toxic salts, starting from an acetoacetyl compound; the process comprises reacting acetoacetamide with at least approximately twice the molar amount of SO$_3$, where appropriate in an inert inorganic or organic solvent, and then, where appropriate, also neutralizing with a base the 6-methyl-3,4-dihydro-1,2,3-oxathiazin-4-one 2,2-dioxide which is produced in the form of the acid in this reaction.

During the reaction, it is probable that acetoacetamide-N-sulfonic acid is formed initially, from 1 mole of acetoacetamide and one mole of SO$_3$, and is then cyclized with another mole of SO$_3$ to give 6-methyl-3,4-dihydro-1,2,3-oxathiazin-4-one 2,2-dioxide:

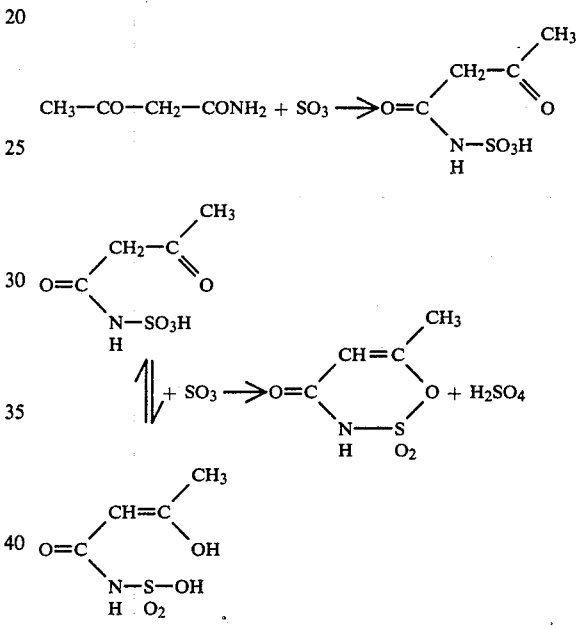

The yields obtained in this reaction are about 30 to about 90% of theory based on acetoacetamide. The process represents a considerable advance in this area, in particular because the starting materials are simple and reasonably priced, and the reaction is extremely straightforward to carry out.

It was very surprising that the reaction took place, in particular the ring closure reaction, because the cyclization, which results in one mole of water being eliminated per mole of acetoacetamide-N-sulfonic acid, does not take place or, at any rate, virtually does not take place with other agents which eliminate water, such as, for example, P$_2$O$_5$, acetic anhydride, trifluoroacetic anhydride, thionyl chloride etc.

Acetoacetamide can be obtained from, for example, acetoacetyl chloride or diketene and NH$_3$ and is, moreover, a readily available commercial product.

The acetoacetamide is then reacted with at least approximately twice the molar amount of SO$_3$ (per mole of acetoacetamide). The amount of SO$_3$ is preferably about 2 to 20 moles, in particular about 4 to 10 moles, per mole of acetoacetamide. It can be added to the reaction mixture either in the solid or liquid form or by condensing in SO$_3$ vapor. However, the more usual mode of addition comprises the addition of a solution of $SO_3$ in concentrated sulfuric acid, liquid $SO_2$ or an inert organic solvent.

It is also possible to use reactive $SO_3$ derivatives which eliminate $SO_3$. It is particularly favorable for the course of the reaction to replace part of the free $SO_3$ by a reactive $SO_3$ derivative. Examples of such reactive $SO_3$ derivatives are adducts of $SO_3$ with tertiary amines or N-alkyl-substituted carboxamides, preferably those tertiary amines in which each N atom has up to 20, in particular up to only 10, carbon atoms. The following tertiary amines may be mentioned as examples:

Trimethylamine, triethylamine, tri-n-propylamine, triisopropylamine, tri-n-butylamine, triisobutylamine, tricyclohexylamine, ethyldiisopropylamine, ethyldicyclohexylamine, N,N-dimethylaniline, N,N-diethylaniline, benzyldimethylamine, pyridine, substituted pyridines, such as picolines, lutidines, collidines or methyl ethyl pyridines, N-methylpiperidine, N-ethylpiperidine, N-methylmorpholine, N,N'-dimethylpiperazine, 1,5-diazabicyclo[4.3.0]non-5-ene, 1,8-diazabicyclo[5.4.0]undec-7-ene, also tetramethylhexamethylenediamine, tetramethylethylenediamine, tetramethylpropylenediamine, tetramethylbutylenediamine, as well as 1,2-dimorpholylethane, pentamethyldiethylenetriamine, pentaethyldiethylenetriamine, pentamethyldipropylenetriamine, tetramethyldiaminomethane, tetrapropyldiaminomethane, hexamethyltriethylenetetramine, hexamethyltripropylenetetramine, diisobutylenetriamine or triisopropylenetetramine.

Particularly favorable reactive $SO_3$ derivatives are: $(CH_3)_3N.SO_3$, $(C_2H_5)_3N.SO_3$, pyridine.$SO_3$, 2-picoline.$SO_3$, 2,6-lutidine.$SO_3$ and collidine.$SO_3$. The adduct $HCON(CH_3)_2.SO_3$, for example, can also be used successfully.

It is also possible to produce the adducts in situ.

Although, in principle, it is possible to carry out the reaction according to the invention without a solvent, nevertheless it is preferable to carry it out in an inert inorganic or organic solvent. Suitable inert inorganic or organic solvents are those liquids which do not react in an undesired manner with $SO_3$ or its reactive derivatives or with acetoacetamide or the final product of the reaction. Thus, because of the considerable reactivity of, in particular, $SO_3$ and its reactive adducts, only relatively few solvents are suitable for this purpose.
Preferred solvents are:
Inorganic solvents: liquid $SO_2$;
organic solvents: halogenated aliphatic hydrocarbons, preferably having up to 4 carbon atoms, such as, for example, methylene chloride, chloroform, 1,2-dichloroethane, trichloroethylene, tetrachloroethylene, chloroethylene, trichlorofluoroethylene etc.;
esters of carbonic acid with lower aliphatic alcohols, preferably with methanol or ethanol;
nitroalkanes, preferably having up to 4 carbon atoms, in particular nitromethane;
pyridine and alkyl-substituted pyridine, preferably collidine; and
aliphatic sulfones, preferably sulfolane.

The organic solvents can be used either alone or in a mixture.

Particularly preferred organic solvents are: methylene chloride, chloroform, 1,2-dichloroethane, dimethyl carbonate, nitromethane and collidine.

The amount of inert solvent used is not critical. When a solvent is used, it is merely necessary to ensure adequate solution of the reactants; the upper limit of the amount of solvent is determined by economic considerations.

The reaction temperature is normally between about $-70°$ and $+180°$ C., preferably between about $-40°$ and $+90°$ C.

The reaction is normally carried out under atmospheric pressure.

The reaction time can be between a few minutes (at higher temperatures) and a few days (in the lower temperature range).

The reaction can be carried out in such a manner that the acetoacetamide, where appropriate in solution, is initially introduced and $SO_3$, or the reactive $SO_3$ adduct, where appropriate in the dissolved form, is metered in, or both reactants are simultaneously transferred into the reaction chamber, or $SO_3$, or its reactive derivatives, is initially introduced and acetoacetamide is fed in, or, for example, acetoacetamide is initially treated with about 1 to 5 moles, preferably with about 1 to 2 moles, of a reactive $SO_3$ derivative (per mole of acetoacetamide) for about 20 minutes to 48 hours, preferably about 30 minutes to 24 hours, at about $-30°$ to $-180°$ C., preferably at about $0°$ to $90°$ C., and this solution is metered into the $SO_3$.

The acetoacetamide is preferably initially reacted with a reactive $SO_3$ derivative. Subsequently, part of the $SO_3$ is initially introduced and then, either continuously or in portions, both the reaction solution of acetoacetamide and the reactive $SO_3$ derivative, together with $SO_3$, are metered in.

After completion of the reaction, the mixture is normally stirred further for about half an hour up to several hours.

The reaction mixture is worked up in a customary manner. In the case where inert organic solvents (which are immiscible with water) are used as the reaction medium, the working up can be carried out as follows, for example: to the solution containing $SO_3$ are added about 10 times the molar amount (based on $SO_3$) of ice or water. This brings about phase separation: the 6-methyl-3,4-dihydro-1,2,3-oxathiazin-4-one 2,2-dioxide which has formed is present mainly in the organic phase. The fractions still present in the aqueous sulfuric acid can be obtained by extraction with an organic solvent such as, for example, methylene chloride or ethyl acetate. The combined organic phases are then, for example, dried with sodium sulfate and evaporated. If it is intended to obtain the free compound, it is purified in a customary manner (preferably by crystallization). The yield is between about 30 and 90% of theory based on acetoacetamide.

However, if it intended to obtain a non-toxic salt of 6-methyl-3,4-dihydro-1,2,3-oxathiazin-4-one 2,2-dioxide, this is followed by neutralization with a base. For this purpose, it is advantageous to neutralize, using an appropriate base, preferably using a potassium base such as, for example $KOH$, $KHCO_3$, $K_2CO_3$, K alcoholates etc., the organic phases which have been combined, dried and evaporated during the course of the working up of the reaction mixture and are in suitable organic solvents such as, for example, alcohols, ketones, esters or ethers, or in water. The oxathiazinone salt then precipitates out in the form of crystals, where appropriate after evaporation of the solution, and can also be recrystallized for purification.

The yield in the neutralization step is virtually 100%.

The Examples which follows are intended to illustrate the invention further. The (invention) examples are followed by a comparison example which shows that acetoacetamide-N-sulfonic acid does not cyclize with agents which eliminate water other than $SO_3$, in this case $P_2O_5$.

EXAMPLE 1

5.1 g (50 mmol) of acetoacetamide in 50 ml of $CH_2Cl_2$ were added dropwise to 8 ml (200 mmol) of liquid $SO_3$ in 50 ml of $CH_2Cl_2$ at $-60°$ C. After 2 hours, 50 ml of ethyl acetate and 50 ml of water were added to the solution. The organic phase was separated off, and the aqueous phase was extracted twice more with ethyl acetate. The combined organic phases were dried over sodium sulfate, evaporated, and the residue was dissolved in methanol. On neutralization of the solution with methanolic KOH, the potassium salt of 6-methyl-3,4-dihydro-1,2,3-oxathiazin-4-one, 2,2-dioxide precipitated out.

Yield: 3.1 g=31%.

EXAMPLE 2

15.9 g (100 mmol) of the pyridine .$SO_3$ complex and 5.1 g (50 mmol) of acetoacetamide in 100 ml of $CH_2Cl_2$ were stirred at room temperature for 17 hours. The mixture was then added dropwise, within 10 minutes, to a solution of 12 ml (300 mmol) of $SO_3$ in 50 ml of $CH_2Cl_2$ at $-30°$ C. 20 Minutes later, the mixture was worked up as in Example 1.

Yield: 7.9 g=79%.

EXAMPLE 3

A solution of 4 ml (100 mmol) of $SO_3$ in 20 ml of $CH_2Cl_2$ was added dropwise to 13.2 ml (110 mmol) of 2,4,6-collidine in 50 ml of $CH_2Cl_2$ at $-40°$ C. The solution was then stirred with 9.1 g (90 mmole) of acetoacetamide at room temperature for 23 hours. This solution was added dropwise, within 1 hour, to 4.4 ml (110 mmol) of $SO_3$ in 200 ml of $CH_2Cl_2$ at $-30°$ C. Over the same period, 4.4 ml portions (110 mmol) of $SO_3$ were added after 12, 24, 36 and 48 minutes. 20 Minutes later, the mixture was worked up as in Example 1, with the addition of 90 ml of $H_2O$.

Yield: 11.8 g=65%.

EXAMPLE 4

A solution of 4 ml (100 mmol) of $SO_3$ in 20 ml of $CH_2Cl_2$ was added dropwise to 15.2 ml (110 mmol) of triethylamine in 50 ml of 1,2-dichloroethane at $-40°$ C. The solution was boiled with 5.1 g (50 mmol) of acetoacetamide for 4 hours. It was then cooled at $-30°$ C., added dropwise, within 1 hour, to a solution of 2.4 ml (60 mmol) of $SO_3$ in 50 ml of $CH_2Cl_2$. Over the same period, 2.4 ml portions (60 mmol) of $SO_3$ were added after 12, 24, 36 and 48 minutes. 20 Minutes later, the mixture was worked up as in Example 1.

Yield: 1 g=10%.

EXAMPLE 5

A solution of 4 ml (100 mmol) of $SO_3$ in 20 ml of $CH_2Cl_2$ was added dropwise to 13.2 ml (110 mmol) of 2,4,6-collidine in 50 ml of $CH_2Cl_2$ at $-40°$ C. After addition of 5.1 g (50 mmol) of acetoacetamide, the mixture was stirred at room temperature for 17 hours. This solution was added dropwise, within 1 hour, to a solution of 2.4 ml (60 mmol) of $SO_3$ in 50 ml of $CH_2Cl_2$ at $-30°$ C. Over the same period, 2.4 ml portions (60 mmol) of $SO_3$ were added after 12, 24, 36 and 48 minutes. 20 Minutes later, the mixture was worked up as in Example 1.

Yield: 9 g=90%.

EXAMPLE 6

A solution of 5.1 g (50 mmol) of acetoacetamide and 6.9 ml of triethylamine in 100 ml of $CH_2Cl_2$ were added dropwise, within 60 minutes, to 8 ml (200 mmol) of liquid $SO_3$ in 150 ml of $CH_2Cl_2$ at $-25°$ C., and the mixture was then stirred at $-25°$ C. for 90 minutes. The working up was carried out as in Example 1.

Yield: 4.1 g=41%.

EXAMPLE 7

The process was carried out as in Example 6, but 16 g (200 mmol) of solid $SO_3$ were used in place of 8 ml (200 mmol) of liquid $SO_3$.

Yield: 3.7 g=37%.

EXAMPLE 8

A solution of 5.1 g (50 mmol) of acetoacetamide in 100 ml of $CH_2Cl_2$ was added dropwise, within 30 minutes, to a mixture of 15.5 ml (250 mmol $SO_3$) of 65% oleum in 150 ml of $CH_2Cl_2$ at $-25°$ C., and the mixture was then stirred at $-25°$ C. for 60 minutes. The working up was carried out as in Example 1.

Yield: 2.3 g=23%.

COMPARISON EXAMPLE 35.42 g (250 mmol) of $P_2O_5$ were initially introduced into 250 ml of $CH_2Cl_2$. At $-25°$ C., 62.5 ml of acetoacetamide-N-sulfonic acid solution in $CH_2Cl_2$, containing 0.05 mole of the sulfonic acid (yields 9 g), were added dropwise within 60 minutes. After a further 60 minutes at $-25°$ C., the mixture was worked up as in Example 1. No 6-methyl-3,4-dihydro-1,2,3-oxathiazin-4one 2,2-dioxide or its potassium salt could be detected in the reaction product by thin-layer chromatography.

We claim:

1. A process for the preparation of 6-methyl-3,4-dihydro-1,2,3-oxathiazin-4-one 2,2-dioxide and its non-toxic salts, which comprises reacting acetoacetamide with at least approximately twice the molar amount of $SO_3$ in an inert inorganic or organic solvent.

2. The process as claimed in claim 1, wherein the amount of $SO_3$ used is about 2 to 20 moles per mole of acetoacetamide.

3. The process as claimed in claim 2, wherein the amount of $SO_3$ used is about 4 to 10 moles per mole of acetoacetamide.

4. The process as claimed in claim 1, wherein part of the $SO_3$ is used in the form of reactive derivatives.

5. The process as claimed in claim 4, wherein the reactive derivatives are tertiary amines.

6. The process as claimed in claim 1, wherein the inert inorganic solvent used is liquid $SO_2$ and the inert organic solvent used is at least one solvent from the following group: halogenated aliphatic hydrocarbons; esters of carbonic acid with lower aliphatic alcohols; nitroalkanes; pyridine and alkyl-substituted pyridines and aliphatic sulfones.

7. The process as claimed in claim 6, wherein the inert inorganic solvent is a halogenated aliphatic hydrocarbon having up to 4 carbon atoms; an ester of carbonic acid with methanol or ethanol; a nitroalkane having up to 4 carbon atoms; pyridine; collidine; or sulfolane.

8. The process as claimed in claim 1, wherein the inert organic solvent used is at least one of the following solvents: ethylene chloride, chloroform, 1,2-dichloroethane, dimethyl carbonate, nitromethane and collidine.

9. The process as claimed in claim 1, wherein the reaction is carried out at temperatures between about −70° and +180° C.

10. The process as claimed in claim 9, wherein the reaction is carried out at temperatures between about −40° and +90° C.

11. The process as claimed in claim 1 including the further step of neutralizing with a base the 6-methyl-3,4-dihydro-1,2,3-oxathiazin-4one 2,2-dioxide which is produced in the form of the acid in this reaction in order to obtain the non-toxic salts.

12. The process as claimed in claim 11, wherein the base used for the neutralization of 6-methyl-3,4-dihydro-1,2,3-oxathiazin-4-one 2,2-dioxide is a potassium base.

* * * * *